United States Patent [19]

Kubo et al.

[11] 4,273,136
[45] Jun. 16, 1981

[54] ELECTRONIC SPHYGMOMANOMETER

[75] Inventors: Kimio Kubo, Nara; Ryuichi Miyamae, Yamatokoriyama, both of Japan

[73] Assignee: Sharp Kabushiki Kaisha, Osaka, Japan

[21] Appl. No.: 963,134

[22] Filed: Nov. 22, 1978

[30] Foreign Application Priority Data

Nov. 24, 1977 [JP] Japan ............................ 52-158002[U]
Nov. 25, 1977 [JP] Japan ............................ 52-158485[U]
Nov. 30, 1977 [JP] Japan ............................ 52-162424[U]

[51] Int. Cl.$^3$ .............................................. A61B 5/02
[52] U.S. Cl. ................................... 128/680; 128/681
[58] Field of Search ............................... 128/680–683

[56] References Cited

U.S. PATENT DOCUMENTS

| | | | |
|---|---|---|---|
| 3,939,824 | 2/1976 | Arreson et al. | 128/672 |
| 4,009,709 | 3/1977 | Link et al. | 128/681 |
| 4,058,117 | 11/1977 | Kaspari et al. | 128/682 |
| 4,105,021 | 8/1978 | Williams et al. | 128/683 |
| 4,116,230 | 9/1978 | Gorelick | 128/682 |
| 4,144,879 | 3/1979 | Nakayama et al. | 128/680 |
| 4,174,707 | 11/1979 | Link et al. | 128/681 |
| 4,190,886 | 2/1980 | Sherman | 128/673 |

OTHER PUBLICATIONS

Looney, J., "Blood Pressure by Oscillometry," *Med. Electronics* Apr. 1978, pp. 57–63.

*Primary Examiner*—Robert W. Michell
*Assistant Examiner*—Francis J. Jaworski
*Attorney, Agent, or Firm*—Birch, Stewart, Kolasch & Birch

[57] ABSTRACT

A blood pressure measurement system comprises a determination means for determining whether a cuff pressure is increasing for preparation purposes or decreasing for measurement purposes. The determination means includes a comparator for comparing the current cuff pressure with the last cuff pressure, and detection means for detecting whether a difference between the current cuff pressure and the last cuff pressure is smaller than a predetermined value. Another determination means is provided for detecting whether the cuff pressure is first increased to a desired level higher than systolic pressure of a person to be measured. A reset means is provided for automatically resetting the system when the cuff pressure is decreased to a predetermined level after completion of measurement.

11 Claims, 5 Drawing Figures

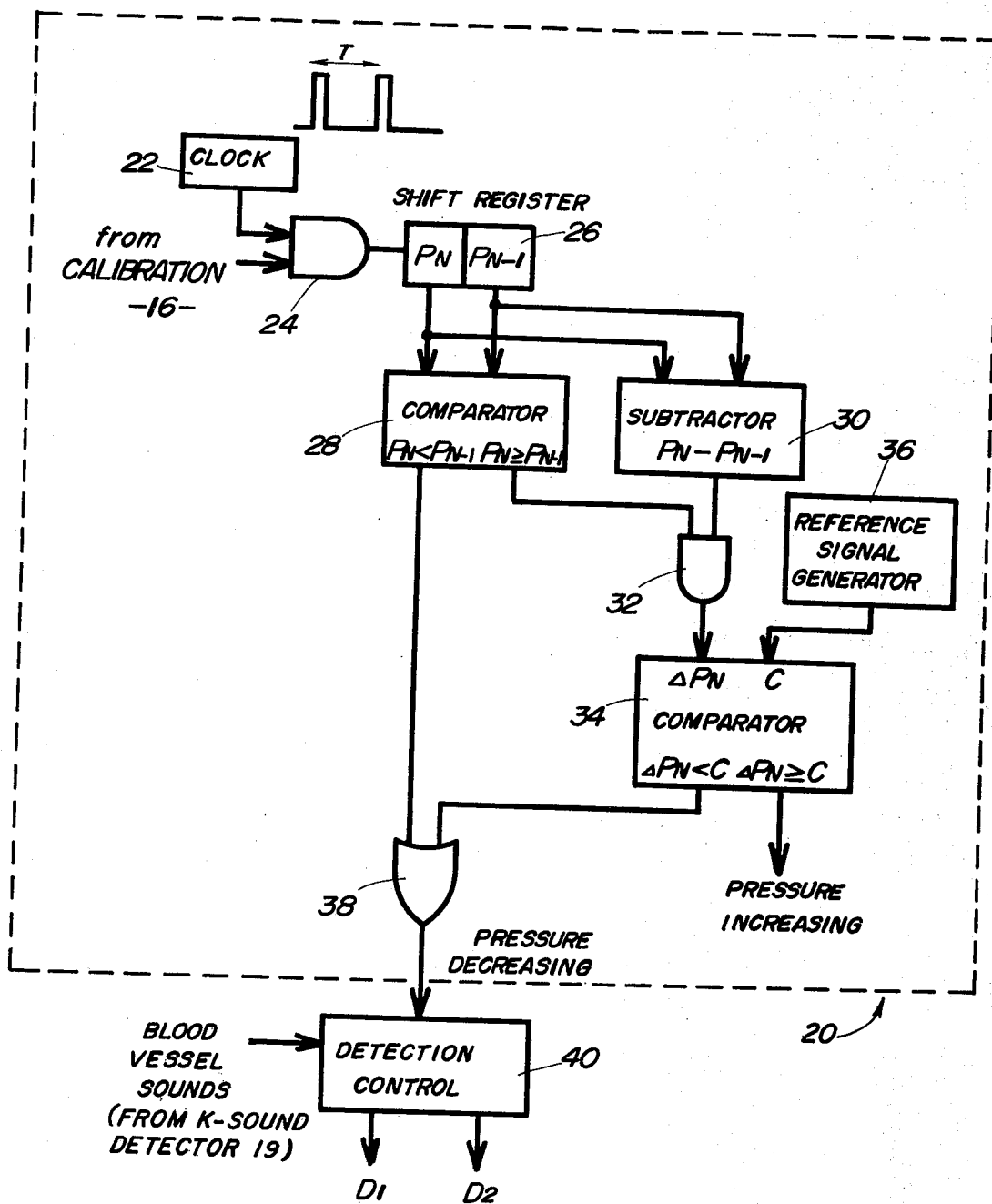
FIG. 3 (UP/DOWN DETERMINATION -20-)

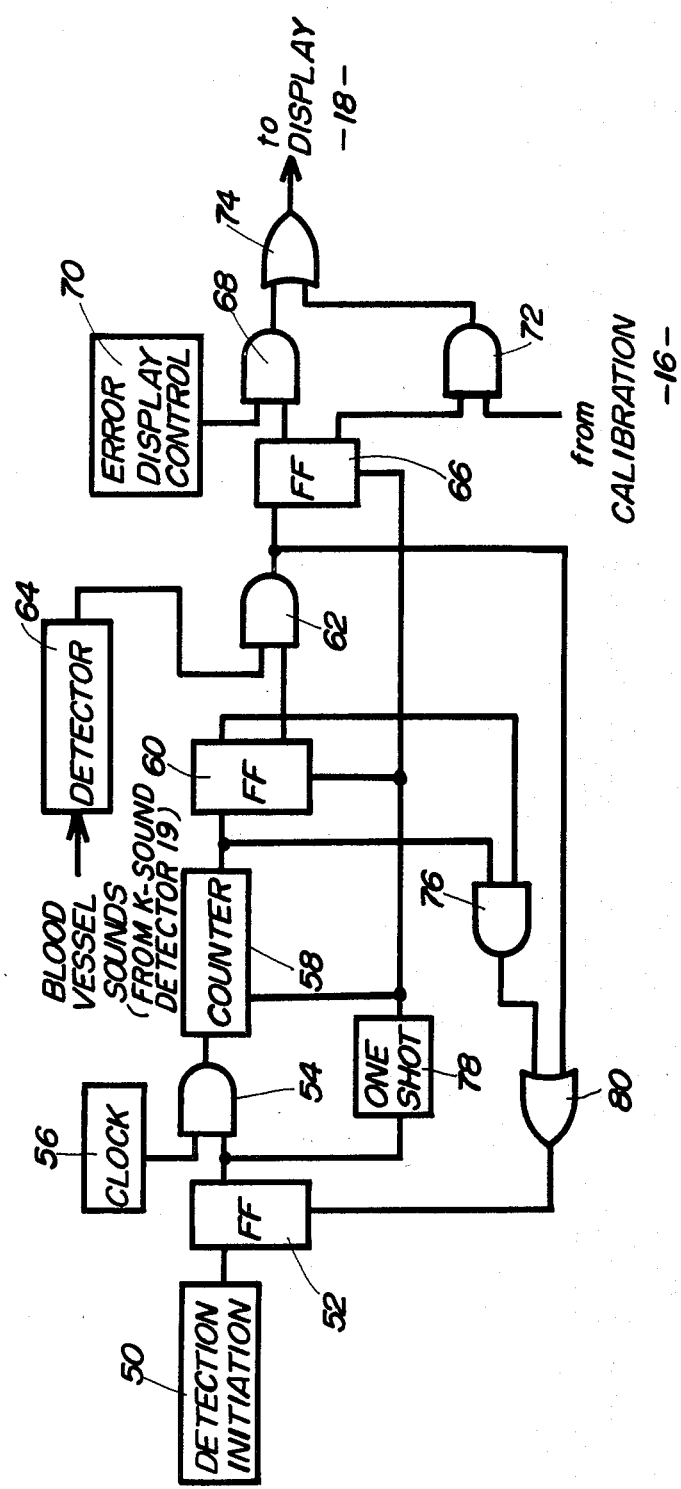
FIG. 4 (STANDBY DETECTION -48-)

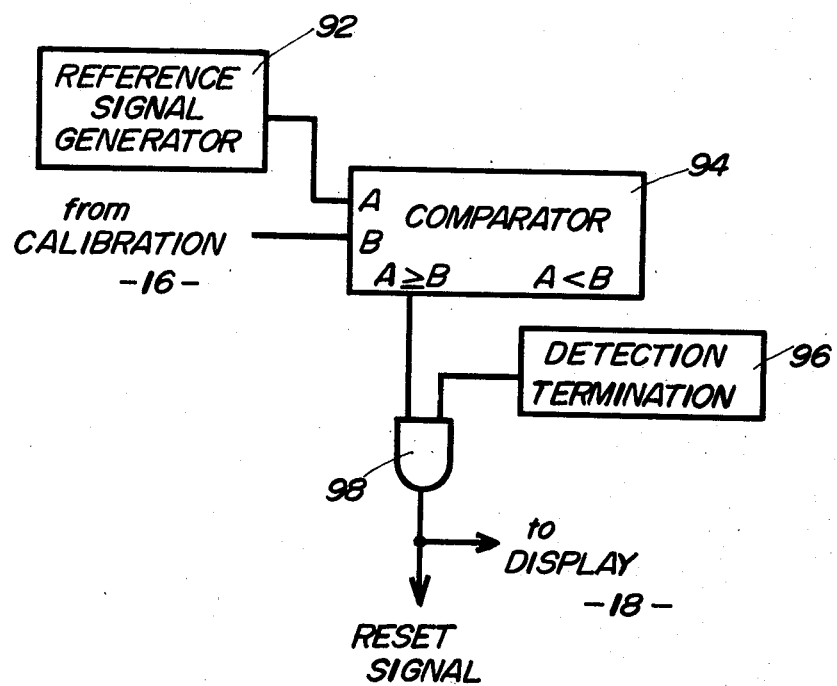
FIG.5 (AUTO RESET -90-)

ELECTRONIC SPHYGMOMANOMETER

BACKGROUND AND SUMMARY OF THE INVENTION

The present invention relates to an electronic sphygmomanometer and, more particularly, to an automatic indirect blood pressure measurement system, which displays systolic and diastolic pressure on a digital display panel.

An automatic indirect blood pressure measurement system has been developed, which utilizes the Korotkoff sounds, or blood vessel sounds derived from a microphone positioned under an arm cuff. In such a system, first a high pressure is applied to the arm cuff through the use of an air pump and, then, the pressure applied to the arm cuff is gradually reduced at a rate, for example, 2 to 4 mmHg/sec. During the reduction procedure of the applied pressure, the Korotkoff sounds appear at the systolic pressure point, and the Korotkoff sounds disappear at the diastolic pressure point.

An automatic measurement of the systolic and diastolic pressure can be conducted by detecting the cuff pressure and the Korotkoff sounds. In the most convenient system, the systolic pressure and the diastolic pressure are displayed on the digital display panel.

To ensure stable operation of the blood pressure measurement system of the above-mentioned type, it is necessary that the cuff pressure is first increased to a level higher than the systolic pressure of a person to be detected. And, the system must correctly detect whether the cuff pressure is increasing for preparation purposes or the cuff pressure is decreasing for measurement purposes.

Accordingly, an object of the present invention is to provide an automatic blood pressure measurement system of stable operation.

Another object of the present invention is to provide an initial condition detection system in an automatic blood pressure measurement system for detecting whether the cuff pressure is first increased to a sufficient level.

Still another object of the present invention is to provide an automatic blood pressure measurement control circuit suited for application of the integrated circuit technique.

Other objects and further scope of applicability of the present invention will become apparent from the detailed description given hereinafter. It should be understood, however, that the detailed description and specific examples, while indicating preferred embodiments of the invention, are given by way of illustration only, since various changes and modifications within the spirit and scope of the invention will become apparent to those skilled in the art from this detailed description.

To achieve the above objects, pursuant to an embodiment of the present invention, the cuff pressure is detected at a predetermined sampling interval. Current cuff pressure is compared with the last cuff pressure in order to determine whether the cuff pressure is increasing for preparation purposes or whether the cuff pressure is decreasing for measurement purposes. Moreover, the difference between the current cuff pressure and the last cuff pressure is calculated. The thus obtained difference is compared with a prefixed value in order to prevent erroneous operation due to fluctuation of the cuff pressure.

In a preferred form, a standby detection circuit is incorporated in the blood pressure measurement system in order to determine whether the cuff pressure is first increased to a desired level greater than the systolic pressure of a person to be measured. More specifically, a time interval detection means is provided for detecting a time interval from initiation of the measuring operation to a time at which the first Korotkoff sound appears. When the Korotkoff sound appears before a predetermined time interval has passed, the standby detection circuit determines that the cuff pressure has not been increased to the desired level.

In another preferred form, an auto reset circuit is incorporated in the blood pressure measurement system, which functions to automatically reset the system when the cuff pressure is reduced to a predetermined value, for example, 20 mmHg.

BRIEF DESCRIPTION OF THE DRAWINGS

The present invention will become more fully understood from the detailed description given hereinbelow and the accompanying drawings which are given by way of illustration only, and thus are not limitative of the present invention and wherein:

FIG. 3 is a block diagram of an up/down determination circuit included in the electronic blood pressure measurement system of FIG. 1;

FIG. 4 is a block diagram of a standby condition detection circuit included in the electronic blood pressure measurement system of FIG. 1; and FIG. 5 is a block diagram of an auto reset circuit included in the electronic blood pressure measurement system of FIG. 1.

DESCRIPTION OF THE PREFERRED EMBODIMENTS

Figure 1:
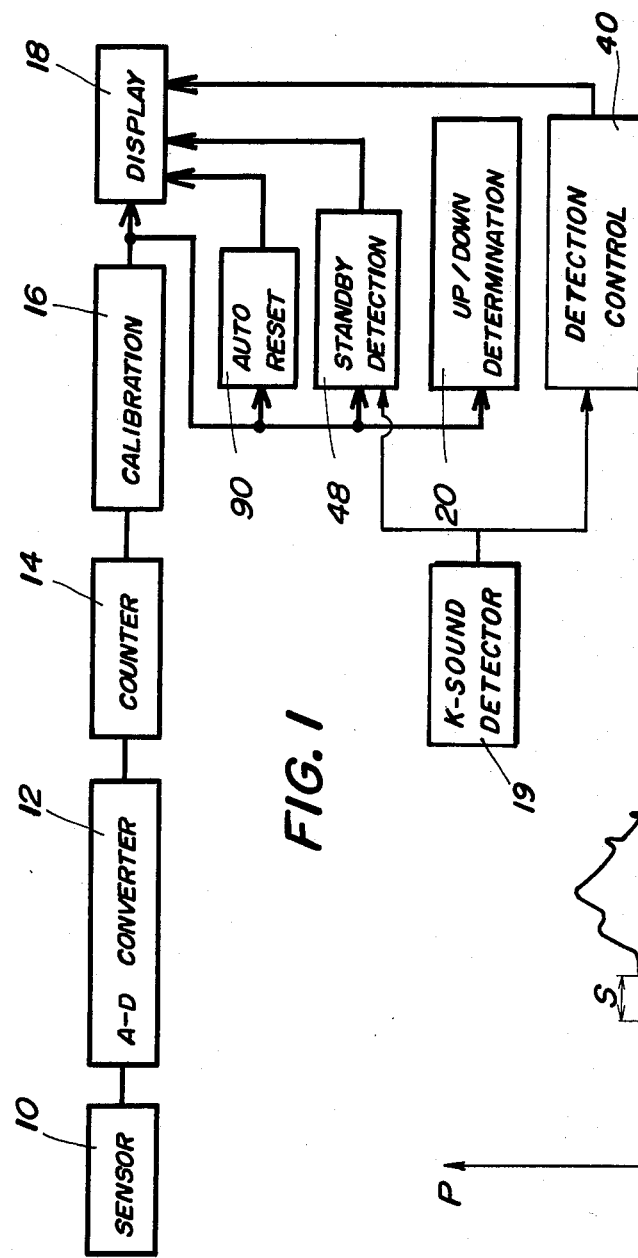
FIG. 1 is a schematic block diagram of an embodiment of an electronic blood pressure measurement system of the present invention.

FIG. 1 schematically shows an embodiment of an electronic blood pressure measurement system of the present invention.

Generally, the electronic blood pressure measurement system comprises a pressure sensor 10 for detecting a cuff pressure. The detected cuff pressure is converted into a pulse signal by an A - D converter 12, the pulse frequency being proportional to the detected cuff pressure. The pulse signal derived from the A - D converter 12 is sampled at a predetermined time interval and counted by a counter 14. A calibration circuit 16 functions to generate an accurate representation of the current cuff pressure through the use of contents stored in the counter 14, thereby indicating systolic pressure and diastolic pressure on a display panel 18 in a digital fashion.

The electronic blood pressure measurement system of the present invention further comprises an up/down determination circuit 20 for determining whether the cuff pressure is increasing for preparation purposes or decreasing for measurement purposes, a standby detection circuit 48 for detecting whether the cuff pressure is first increased to a level higher than the systolic pressure of a person to be measured, and an auto reset circuit 90 for automatically resetting the system when the pressure measurement is completed. A K-sound detector 19 applies a signal representative of blood pressure sounds to the Up/Down determination circuit 20 and the standby detection circuit 48.

In the automatic blood pressure measurement system, it is necessary to correctly determine whether the cuff pressure is increasing for preparation purposes or the cuff pressure is decreasing for measurement purposes.

Figure 2:
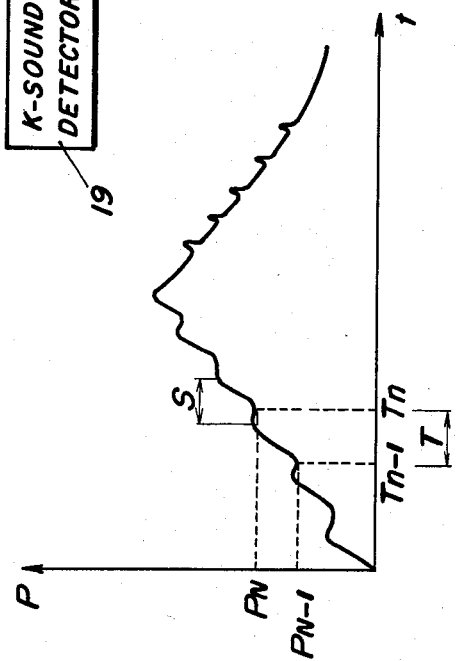
FIG. 2 is a graph showing cuff pressure variations.

FIG. 2 shows variations of the cuff pressure.

The cuff pressure is first increased to a desired level through the use of an air pump. The fluctuation is observed in the increasing curve due to the pump characteristic. It will be clear from FIG. 2 that there is a decreasing section even in the increasing curve. Such a decreasing section must be ignored by a detection system to ensure stable operation. During the measuring operation, the cuff pressure is gradually decreased. The fluctuation is also observed in the decreasing curve due to the blood pressure pulsation. That is, there is an increasing section even in the decreasing curve. Such an increasing section must be ignored by the detection system to ensure stable operation.

A cuff pressure sampling interval T is selected longer than the fluctuation interval S to ensure stable operation. Moreover, not only the current cuff pressure is compared with the last cuff pressure but the difference between the current cuff pressure and the last cuff pressure is examined in the blood pressure measurement system of the present invention.

FIG. 3 shows the up/down determination circuit 20.

The output signal of the calibration circuit 16 is introduced into one input terminal of an AND gate 24. The other input terminal of the AND gate 24 receives a clock signal derived from a clock generator 22, which determines the sampling interval T. In a preferred form, the sampling interval T is about 0.7 to 0.8 seconds. An output signal of the AND gate 24 is applied to a shift register 26, which includes two storage sections $P_N$ and $P_{N-1}$. The current cuff pressure data are stored in the section $P_N$, and the last cuff pressure data are stored in the section $P_{N-1}$.

The data stored in the sections $P_N$ and $P_{N-1}$ are introduced into a comparator 28 and a subtractor 30. The comparator 28 functions to compare the current cuff pressure with the last cuff pressure. When the current cuff pressure is smaller than the last cuff pressure ($P_N < P_{N-1}$) the comparator 28 develops a pressure decreasing detection signal toward an OR gate 38. Contrarily, when the current cuff pressure is greater than or equal to the last cuff pressure ($P_N \geq P_{N-1}$), the comparator 28 develops a detection signal toward an AND gate 32. The subtractor 30 functions to conduct the calculation $P_N - P_{N-1}$.

When the current cuff pressure is greater than the last cuff pressure, the difference ($P_N - P_{N-1}$) calculated by the subtractor 30 is applied to one input terminal $\Delta P_N$ of a comparator 34 through the AND gate 32. Another input terminal C of the comparator 34 receives reference data, for example, 5 mmHg derived from a reference signal generator 36.

In case where the difference ($P_N - P_{N-1}$) is greater than the reference data derived from the reference signal generator 36, that is, $\Delta P_N \geq C$, a pressure increasing detection signal is developed from the comparator 34. In case where the difference ($P_N - P_{N-1}$) is smaller than the reference data derived from the reference signal generator 36, that is, $\Delta P_N < C$, the comparator 34 develops the pressure decreasing detection signal toward the OR gate 38.

The thus obtained pressure decreasing detection signal is applied to a detection control circuit 40 through the OR gate 38, whereby the system is placed in the blood pressure measuring mode. The detection control circuit 40 is operative only when the pressure decreasing detection signal is applied thereto, and functions to develop a systolic pressure display control signal $D_1$ when the first Korotkoff sound appears, and to develop a diastolic pressure display control signal $D_2$ when the Korotkoff sounds disappear.

To ensure correct measurement, the cuff pressure must be first increased to a level higher than the systolic pressure of a person to be measured.

FIG. 4 shows the standby detection circuit 48, which determines that the cuff pressure has not been increased to a desired level if the Korotkoff sounds are detected before two seconds have passed from the initiation of the measurement operation.

The standby detection circuit 48 mainly comprises flip-flops 52 and 66 which are initially in the reset states. After increasing the cuff pressure by the air pump, a measurement initiation switch is actuated, whereby a detection initiation circuit 50 develops a measurement initiation signal to set the flip-flop 52.

The set output signal of the flip-flop 52 is applied to a one-shot pulse generator 78, which develops a reset pulse toward a counter 58, a flip-flop 60 and the flip-flop 66. Under these conditions, the output signal of the calibration circuit 16 is applied to the display panel 18 through an AND gate 72 and an OR gate 74. The counter 58 receives a clock signal derived from a clock generator 56 through the AND gate 54 when the flip-flop 52 is in the set state. The counter 58 is constructed to develop a standby signal when the counter 58 counts the clock signal by the number corresponding to a time interval of two seconds. The thus developed standby signal is applied to the flip-flop 60 to set it, and to the flip-flop 52 through an AND gate 76 and an OR gate 80 to reset the flip-flop 52. Under these conditions, the blood pressure measurement system is placed in the normal operation mode.

When the Korotkoff sound is detected by a detector 64 before two seconds have passed from the actuation of the measurement initiation switch, the detector 64 develops a signal, which is applied to the flip-flop 66 through an AND gate 62 to turn set the flip-flop 66. Accordingly, the AND gate 72 is placed in the nonconductive condition and, therefore, the cuff pressure data derived from the calibration circuit 16 are not applied to the display panel 18. The set output signal of the flip-flop 66 is applied to an AND gate 68. The AND gate 68 transfers an error mark display control signal derived from an error display control circuit 70 to the display panel 18 in order to display an error mark "E" on the display panel 18.

The signal derived from the detector 64 is also applied to the reset input terminal of the flip-flop 52 through the AND gate 62 and the OR gate 80. The reset state of the flip-flop 52 is maintained till the next measurement initiation signal is derived from the detection initiation circuit 50.

FIG. 5 shows the auto circuit 90, which mainly comprises a comparator 94.

The cuff pressure data derived from the calibration circuit 16 are applied to one input terminal B of the comparator 94. The other input terminal A of the comparator 94 receives a constant value derived from a reference signal generator 92. A preferred constant value is about 20 mmHg.

The comparator 94 functions to compare the current cuff pressure with the constant value to develop a control signal to an AND gate 98 when the cuff pressure becomes lower than the constant value. The other input terminal of the AND gate 98 receives a measurement termination indication signal derived from a measurement termination detection circuit 96. The measurement termination indication signal can be obtained through the use of the diastolic pressure display control signal $D_2$ derived from the detection control circuit 40.

An output signal of the AND gate 98 is applied to the entire system as an automatic reset signal. The reset signal may be applied to the display panel 18 to indicate the completion of the measurement.

The invention being thus described, it will be obvious that the same may be varied in many ways. Such variations are not to be regarded as a departure from the spirit and scope of the invention, and all such modifications are intended to be included within the scope of the following claims.

What is claimed is:

1. A blood pressure measurement system including a pressure cuff comprising:
   a sensor for detecting a cuff pressure having applied and pulsatile components;
   means for providing blood pressure data derived from said sensor, said blood pressure data including data representative of successive sampled cuff pressures; and
   applied cuff pressure change determination means for determining whether the applied component of said cuff pressure is increasing for preparation purposes or decreasing for measurement purposes, said determination means including;
   comparing means for comparing the current sampled cuff pressure with the last sampled cuff pressure;
   detecting means for detecting and producing an enabling signal when the difference between the current sampled cuff pressure and the last sampled cuff pressure is smaller than a predetermined value; and
   means responsive to said enabling signal for developing a blood pressure measurement mode signal to enable blood pressure determination when said enabling signal is produced by said detecting means.

2. The blood pressure measurement system of claim 1, wherein said detecting means comprises:
   a subtractor for calculating said difference between the current sampled cuff pressure and the last sampled cuff pressure; and
   a comparator for comparing an output signal of said subtractor with a reference value derived from a reference value generator.

3. The blood pressure measurement system of claim 2, wherein said reference value is about 5 mmHg.

4. The blood pressure measurement system of claim 1, 2 or 3, which further comprises:
   a Korotkoff sound detector for developing a detection signal when a Korotkoff sound is detected by a microphone positioned under a cuff; and a display control signal for developing a systolic pressure display control signal when a first detection signal is developed from said Korotkoff sound detector under provision of said blood pressure measurement mode signal, and for developing a diastolic pressure display control signal when said detection signal disappears.

5. The blood pressure measurement system of claim 1, 2 or 3, wherein said determination means further comprises:
   a shift register for temporarily storing said current sampled cuff pressure and said last sampled cuff pressure; and
   means for applying data stored in said shift register to said comparing means and said detecting means.

6. A blood pressure measurement system comprising:
   a pressure cuff;
   a cuff pressure sensor;
   a systolic and diastolic pressure determination circuit; and
   a cuff pressure change determination means for enabling said systolic and diastolic pressure determination circuit, said cuff pressure change determination means including;
   means for sampling successive cuff pressures generated by said cuff pressure sensor;
   a first comparator for comparing a current sampled cuff pressure from said means for sampling with a previously sampled cuff pressure, said first comparator enabling said systolic and diastolic pressure determination circuit when said current sampled cuff pressure is less than said previously sampled cuff pressure;
   a subtractor for generating a difference signal indicative of the difference between said current sampled cuff pressure and said previously sampled cuff pressure;
   a second comparator for comparing the difference signal generated by said subtractor with a reference value signal, said second comparator enabling said systolic and diastolic determination circuit when said difference signal is less than said reference signal.

7. The blood pressure system of claim 6, wherein said first comparator inhibits said second comparator when said systolic and diastolic pressure determination circuit is enabled.

8. A blood pressure measurement system comprising:
   a pressure cuff;
   a cuff pressure sensor;
   a systolic and diastolic pressure determination circuit; and
   a cuff pressure change determination means for enabling said systolic and diastolic pressure determination circuit, said cuff pressure change determination means including;
   means for sampling successive cuff pressures generated by said cuff pressure sensor;
   first comparator means for comparing a current sampled cuff pressure from said means for sampling with a previously sampled cuff pressure, said first comparator means enabling said systolic and diastolic pressure determination circuit when said current sampled cuff pressure is less than said previously sampled cuff pressure;
   second comparator means for calculating the difference between said current sampled cuff pressure and said previously sampled cuff pressure and comparing the calculated difference with a reference value, said second comparator means enabling said systolic and diastolic pressure determination circuit when said calculated difference is less than said reference value.

9. The blood pressure system of claim 8, wherein said first comparator means disables said second comparator means when said systolic and diastolic pressure determination circuit is enabled.

10. A blood pressure measurement system comprising:
- a pressure cuff;
- a cuff pressure sensor for sensing a cuff pressure having applied and pulsatile components;
- a systolic and diastolic pressure determination circuit; and
- an applied cuff pressure change determination means for determining whether the applied component of said cuff pressure is increasing for preparation purposes or decreasing for measurement purposes and for enabling said systolic and diastolic pressure determination circuit, said cuff pressure change determination means including;
- means for sampling successive cuff pressures generated by said cuff pressure sensor; and
- comparator means for enabling said systolic and diastolic pressure determination circuit when the current sampled cuff pressure is less than a reference value greater than the previously sampled cuff pressure.

11. The blood pressure measurement system of claims 6, 8, or 10, wherein said reference value is about 5 mm Hg.

* * * * *